United States Patent
Hyun et al.

(10) Patent No.: US 8,111,892 B2
(45) Date of Patent: Feb. 7, 2012

(54) REGISTRATION OF CT IMAGE ONTO ULTRASOUND IMAGES

(75) Inventors: Dong Gyu Hyun, Seoul (KR); Jong Beom Ra, Daejeon (KR); Duhgoon Lee, Daejeon (KR); Woo Hyun Nam, Busan (KR); Dong-Goo Kang, Suwon-si (KR)

(73) Assignees: Medison Co., Ltd., Kangwon-Do (KR); Korea Advanced Institute of Science and Technology, Daejeon (KR)

( * ) Notice: Subject to any disclaimer, the term of this patent is extended or adjusted under 35 U.S.C. 154(b) by 402 days.

(21) Appl. No.: 12/476,153

(22) Filed: Jun. 1, 2009

(65) Prior Publication Data

US 2009/0303252 A1   Dec. 10, 2009

(30) Foreign Application Priority Data

Jun. 4, 2008   (KR) ................ 10-2008-0052652

(51) Int. Cl.
*G06K 9/00* (2006.01)
(52) U.S. Cl. .................................. 382/131; 382/128
(58) Field of Classification Search .............. 382/128, 382/131
See application file for complete search history.

(56) References Cited

U.S. PATENT DOCUMENTS

| | | | |
|---|---|---|---|
| 2004/0122325 A1 | 6/2004 | Chambers et al. | |
| 2006/0004275 A1* | 1/2006 | Vija et al. | 600/407 |
| 2007/0010743 A1 | 1/2007 | Arai | |
| 2008/0009699 A1* | 1/2008 | Sakas et al. | 600/407 |
| 2009/0054772 A1* | 2/2009 | Lin et al. | 600/439 |
| 2009/0067752 A1 | 3/2009 | Lee et al. | |
| 2010/0036247 A1 | 2/2010 | Yamamoto et al. | |

FOREIGN PATENT DOCUMENTS

| | | |
|---|---|---|
| JP | 2002-112998 | 4/2002 |
| JP | 2006-068102 | 3/2006 |
| JP | 2007-054641 | 3/2007 |
| JP | 2007-275440 A | 10/2007 |
| JP | 2009-071821 | 4/2009 |

(Continued)

OTHER PUBLICATIONS

Pitiot et al., "Piecewise Affine Registration of Biological Images for Volume Reconstruction," Medical Image Analysis, Elsevier, 19 pages (Received Aug. 9, 2004).

(Continued)

*Primary Examiner* — Roy M Punnoose
(74) *Attorney, Agent, or Firm* — McDermott Will & Emery LLP (57) ABSTRACT

Embodiments for registering a CT image onto ultrasound images are disclosed. At a preoperative stage, a plurality of first ultrasound images are formed during a respiratory cycle and a CT image is obtained at the maximum inspiration. The CT image is registered onto each of the ultrasound images to thereby form ultrasound-CT registered images. The ultrasound-CT registered images may be stored in the storage unit. Subsequently, at an intraoperative stage, a plurality of second ultrasound images may be sequentially formed in real time. Similarities may be measured between the first ultrasound images and the second ultrasound images, and the ultrasound-CT registered images, each corresponding to each of the first ultrasound images having highest similarity to the second ultrasound image may be retrieved. The retrieved ultrasound image and the second ultrasound image may be displayed at the same time.

20 Claims, 7 Drawing Sheets

FOREIGN PATENT DOCUMENTS

| WO | WO 02/09588 A1 | 2/2002 |
| WO | WO 2004/098414 A1 | 11/2004 |
| WO | WO 2006/064676 A1 | 6/2006 |

OTHER PUBLICATIONS

Xu, Sheng, et al., "Closed-Loop Control in Fused MR-TRUS Image-Guided Prostate Biopsy", 2007, pp. 128-135, Part I. LNCS 4791, MICCAI 2007, Ayache, N., et al (Eds.), Springer-Verlag Berlin Heidelberg.

Huang, Xishi, et al., "Dynamic 3D Ultrasound and MR Image Registration of the Beating Heart", 2005, pp. 171-178, LNCS 3750, MICCAI 2005, Duncan, J., et al. (Eds.), Springer-Verlag Berlin Heidelberg.

Blackall, Jane M., et al., "Alignment of Sparse Freehand 3-D Ultrasound With Preoperative Images of the Liver Using Models of Respiratory Motion and Deformation", Nov. 2005, pp. 1405-1416, IEEE Transactions of Medical Imaging, vol. 24, No. 11.

Lindseth, Frank, et al., "Multimodal image fusion in ultrasound-based neuronavigation: improving overview and interpretation by integrating preoperative MRI with intraoperative 3D ultrasound", Jan. 1, 2003, vol. 8 No. 2, pp. 1-30, Biomedical paper.

Extended European Search Report, issued in European Patent Application No. 09 007 286.9, dated Nov. 4, 2011.

* cited by examiner

REGISTRATION OF CT IMAGE ONTO ULTRASOUND IMAGES

The present application claims priority to Korean Patent Application No. 10-2008-0052652 filed on Jun. 4, 2008, the entire subject matter of which is incorporated herein by reference.

TECHNICAL FIELD

The present disclosure relates to image registrations, and more particularly to the registration of a computerized-tomography (CT) image onto ultrasound images.

BACKGROUND

Surgical treatment using a medical needle such as ablator or biopsy has recently become popular due to relatively small incisions made in such a procedure. The surgical treatment is performed by inserting the medical needle into an internal region of a human body while referring to an internal image of the human body. Such surgical treatment, which is performed while observing internal organs of the human body with the help of a diagnostic imaging system, is referred to as an interventional treatment. The interventional treatment is performed by directing the medical needle to the lesion to be treated or examined through a skin with reference to images during the treatment. The images are acquired by employing a computerized tomography (CT) scanner generally used in a radiology department or a magnetic resonance imaging (MRI) system. Compared to a normal surgical treatment requiring relatively wide incisions to open the lesion, the interventional treatment has the advantages of low costs and obtaining effective operation results. This is because general anesthesia is not necessary for the interventional treatment and patients are subjected to less pain while benefiting from rapid recovery.

However, the CT has problems since it is difficult to obtain an image in real time. Further, an operator and a patient may be exposed to radiation for a long time during the interventional treatment. Compared to the interventional treatment using the CT, an ultrasound diagnostic system may obtain an image in real time and is relatively harmless. However, it is difficult to examine all the lesions of a patient through the ultrasound image. Also, since a viewing angle of the ultrasound diagnostic system is relatively narrow, only a portion of a lesion may be obtained. That is, neighboring regions, which are used for tracing a path of the lesion, cannot be obtained with the target object. Further, a signal to noise ratio of the ultrasound image is low. Thus, it is not possible to practice the interventional treatment with mere reference to ultrasound images.

SUMMARY

Embodiments for registering a CT image onto ultrasound images are disclosed. In one embodiment, by way of non-limiting example, a system for registering a computerized tomography (CT) image to ultrasound images, comprises: an ultrasound image forming unit configured to sequentially form a plurality of first ultrasound images during a predetermined cycle at a preoperative stage; a CT image forming unit configured to provide a CT image obtained at a predetermined time of the predetermined cycle; a registration unit configured to register the CT image to the ultrasound images to thereby form ultrasound-CT registered images; a storage unit configured to store the ultrasound-CT registered images, wherein the ultrasound forming unit is further configured to form a plurality of second ultrasound images in real time at an intraoperative stage, and wherein the registration unit is further configured to measure a similarity between the first ultrasound images and the second ultrasound images and retrieve an ultrasound-CT registered image corresponding to a first ultrasound image having a highest similarity to the second ultrasound image; and a display unit configured to display the retrieved ultrasound image and the second ultrasound image.

In another embodiment, a method of registering a computerized tomography (CT) image to ultrasound images, comprises: a) sequentially forming a plurality of first ultrasound images during a predetermined cycle at a preoperative stage; b) providing a CT image obtained at a predetermined time of the predetermined cycle; c) registering the CT image to the ultrasound images to thereby form ultrasound-CT registered images; d) storing the ultrasound-CT registered images; e) forming a plurality of second ultrasound images in real time at an intraoperative stage; f) measuring a similarity between the first ultrasound images and the second ultrasound images and retrieving an ultrasound-CT registered image corresponding to a first ultrasound image having a highest similarity to the second ultrasound image; and g) displaying the retrieved ultrasound image and the second ultrasound image.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
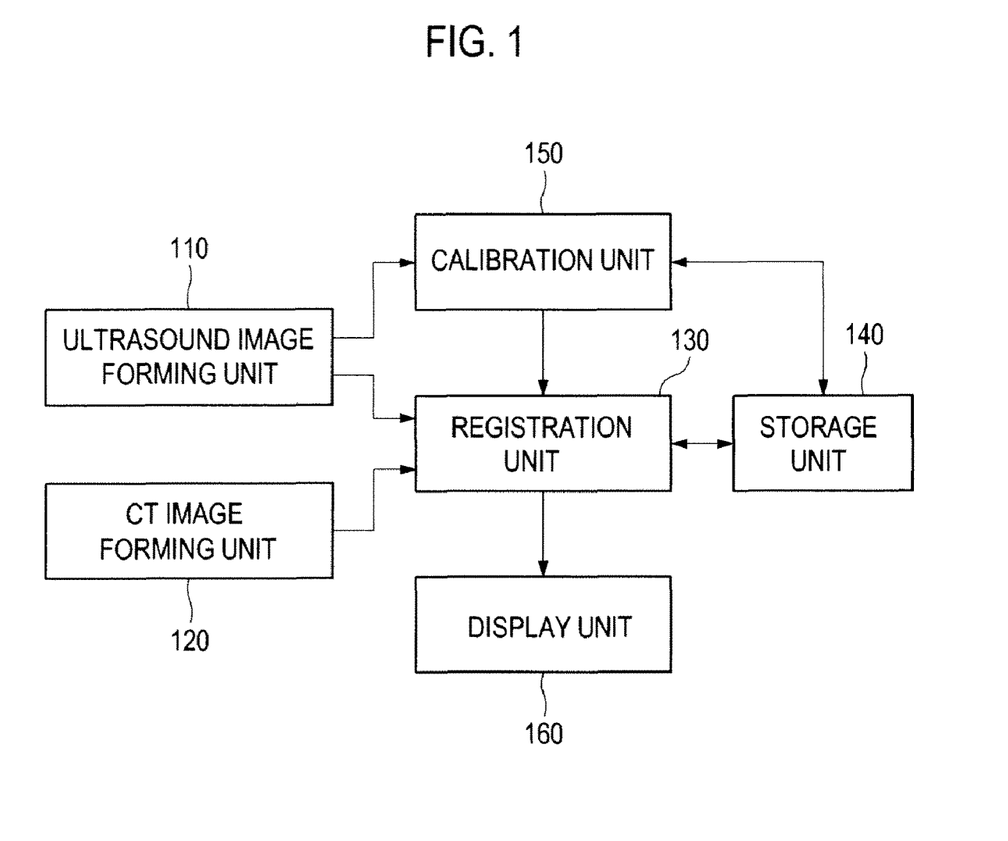
FIG. 1 is a block diagram showing an illustrative embodiment of a system for registering a CT image to ultrasound images.

In one embodiment, ultrasound-computerized tomography (CT) image registration will be described. As depicted in FIG. 1, a system 100 may include an ultrasound image forming unit 110 and a CT image forming unit 120. The ultrasound image forming unit 110 may include a probe (not shown) for transmitting and receiving ultrasound signals.

At a preoperative stage, the ultrasound image forming unit 110 may be configured to sequentially form ultrasound images at a predetermined interval. For example, the ultrasound image forming unit 110 may be configured to repeat forming the ultrasound image during a first period while the probe is placed at a first position on a target object. The CT image forming unit 120 may form a CT image of the target object. In one embodiment, the CT image may be obtained at the maximum inspiration.

The system 100 may further include a registration unit 130 that may be configured to register the CT image to each of the ultrasound images. The registered CT-ultrasound images may be stored in a storage unit 140. At an intraoperative stage, the probe may be moved to a second position adjacent to the first position. The system 100 may further include a calibration unit 150 for establishing a rigid motion calibration function to calibrate the probe movement from the first position to the second position. The calibration function may be applied to the registered ultrasound-CT images.

Figure 2:
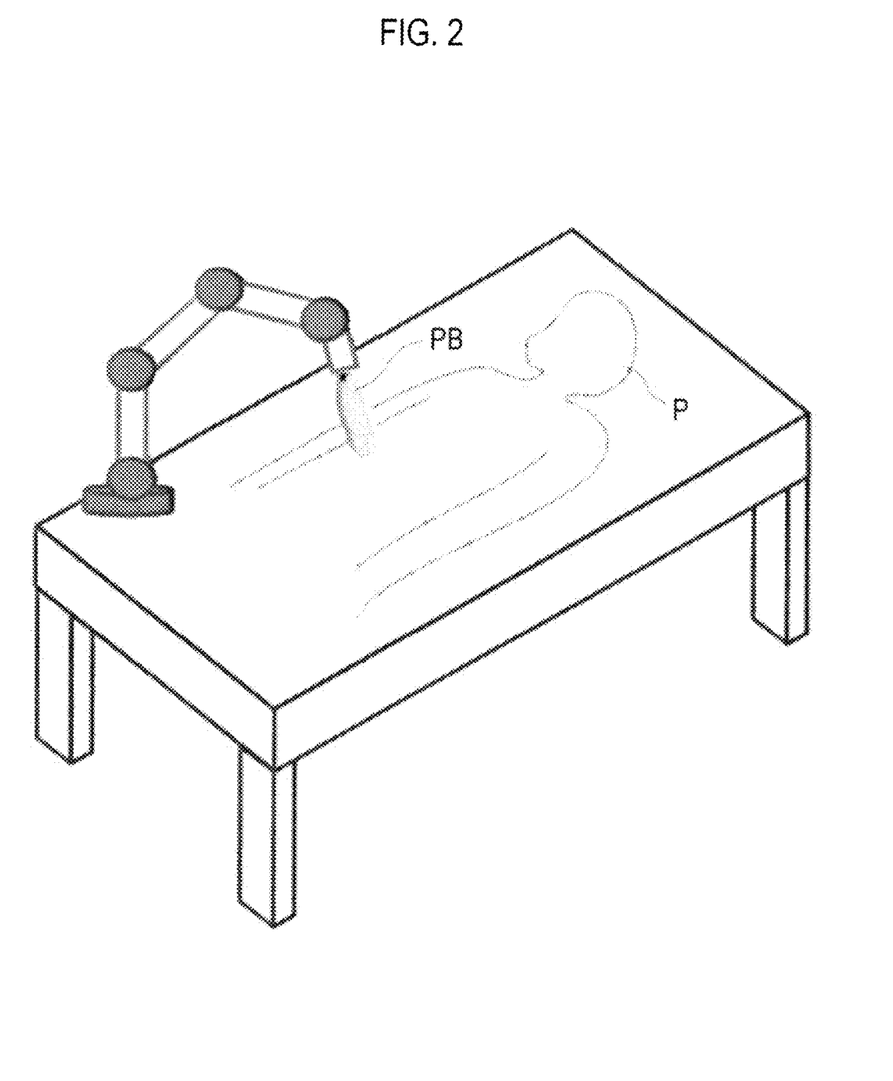
FIG. 2 is a schematic diagram showing an example of a probe placed over a patient.

In one embodiment, the ultrasound image forming unit 10 may be configured to consecutively form 3-dimensional ultrasound images $I_{US}(t_i)$ representative of the target object at a predetermined interval, wherein i is a positive integer and $1 \leq i \leq N$, during a half respiratory cycle representing from the inspiration up to the expiration at the preoperative stage. The CT image forming unit 120 may be also configured to provide the CT image $I_{CT}$ at the preoperative stage. The ultrasound image forming unit 110 may form the 3-dimensional ultrasound image $I_{US}(t_i)$ at the brightness-mode (B-mode). The ultrasound image forming unit 110 may form the 3-dimensional ultrasound images $I_{US}(t_i)$ while the probe PB is fixed at the first position on a patient P, as illustrated in FIG. 2.

In one embodiment, the target object may be a liver, which may be moved according to the respiration. For example, the liver may move about 30 mm for a half respiratory cycle (about 2 seconds) on average. Assuming that a permissible error for the ultrasound-CT registration is 2 mm, a required volume rate of the 3-dimensional ultrasound images may be over $1/[2 \text{ mm} \div (2 \text{ s}/30 \text{ mm})] \cong 8$ vol/s. That is, the required number of the volumes obtained for the half respiratory cycle, i.e., the required number of the 3-dimensional ultrasound images $I_{US}(t_i)$, may be over 16.

Hereinafter, an operation of the registration unit 130 will be described by referring to FIGS. 3 and 4. Once the ultrasound image forming unit 110 completes the formation of the 3-dimensional ultrasound images $I_{US}(t_i)$ and the CT image forming unit 120 provides the CT image $I_{CT}$ at block 310-330, a transform T for the registration of the CT image $I_{CT}$ to the 3-dimensional ultrasound images $I_{US}(t_i)$ is initialized at block 340. In one embodiment, the initial transform $T_{initial}(t_i)$ may be set to a transform $T(t_{i-1})$ previously used to register a CT image $I_{CT}$ onto an ultrasound image $I_{US}(t_{i-1})$. That is, the previous transform $T(t_{i-1})$ may be used as a current transform $T(t_i)$ for the ultrasound-CT registration. The transform $T(t_i)$ at subsequent respiration intervals may be similar to each other. Thus, if the previous transform $T(t_{i-1})$ resulting from the previous registration is used as the current transform $T(t_i)$, then it may be advantageous for an appropriate and robust final transform.

After initializing the transform $T_{initial}(t_i)$, affine registration may be carried out for each interval of the respiration at block 350. In order to perform the affine registration, a set of common feature points may be first extracted from the ultrasound images $I_{US}(t_i)$ and the CT image $I_{CT}$. Then, an affine transform function $T_{affine}$ may be established with the iterative closet point (ICP) algorithm using the set of the feature points. Referring once again to FIG. 3, after performing the affine registration at block 350, local registration for predicting a local motion, which may not be predicted through the affine registration, may be carried out at block 360.

Figure 5:
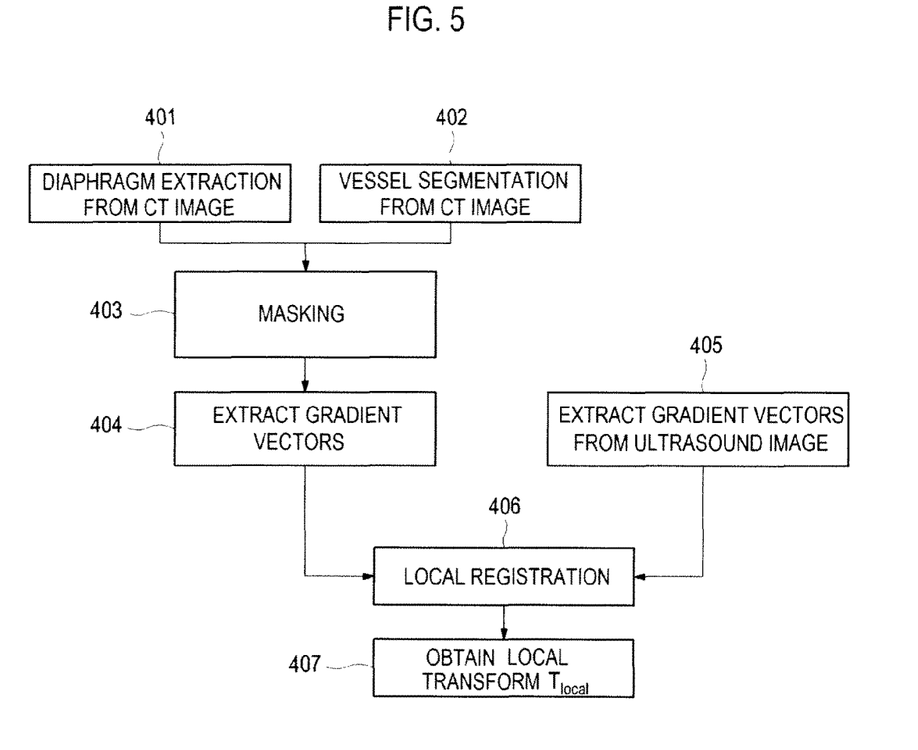
FIG. 5 is a flowchart showing an example of establishing a local registration function.

Referring to FIG. 5, for the local registration of the CT image onto the ultrasound images in one embodiment, diaphragm extraction and vessel segmentation may be carried out upon the CT image at blocks 401 and 402. Further, a masking process for selecting boundary regions is carried out based on the information obtained through the diaphragm extraction and the vessel segmentation at block 403. Gradient vectors may be extracted from the masked CT image and the B-mode ultrasound images at block 404 and 405. The similarity may be measured based on the gradient vectors and brightness values obtained from each image to perform the local registration at block 406 and to obtain a local transform function $T_{local}$ at block 407. The local transform function $T_{local}$ may be defined by using the B-spline free-form deformation (FFD). The smoothness constraint based on a bending energy of a thin-plate of metal may be imposed so as to plate the local transformation $T_{local}$.

Figure 3:
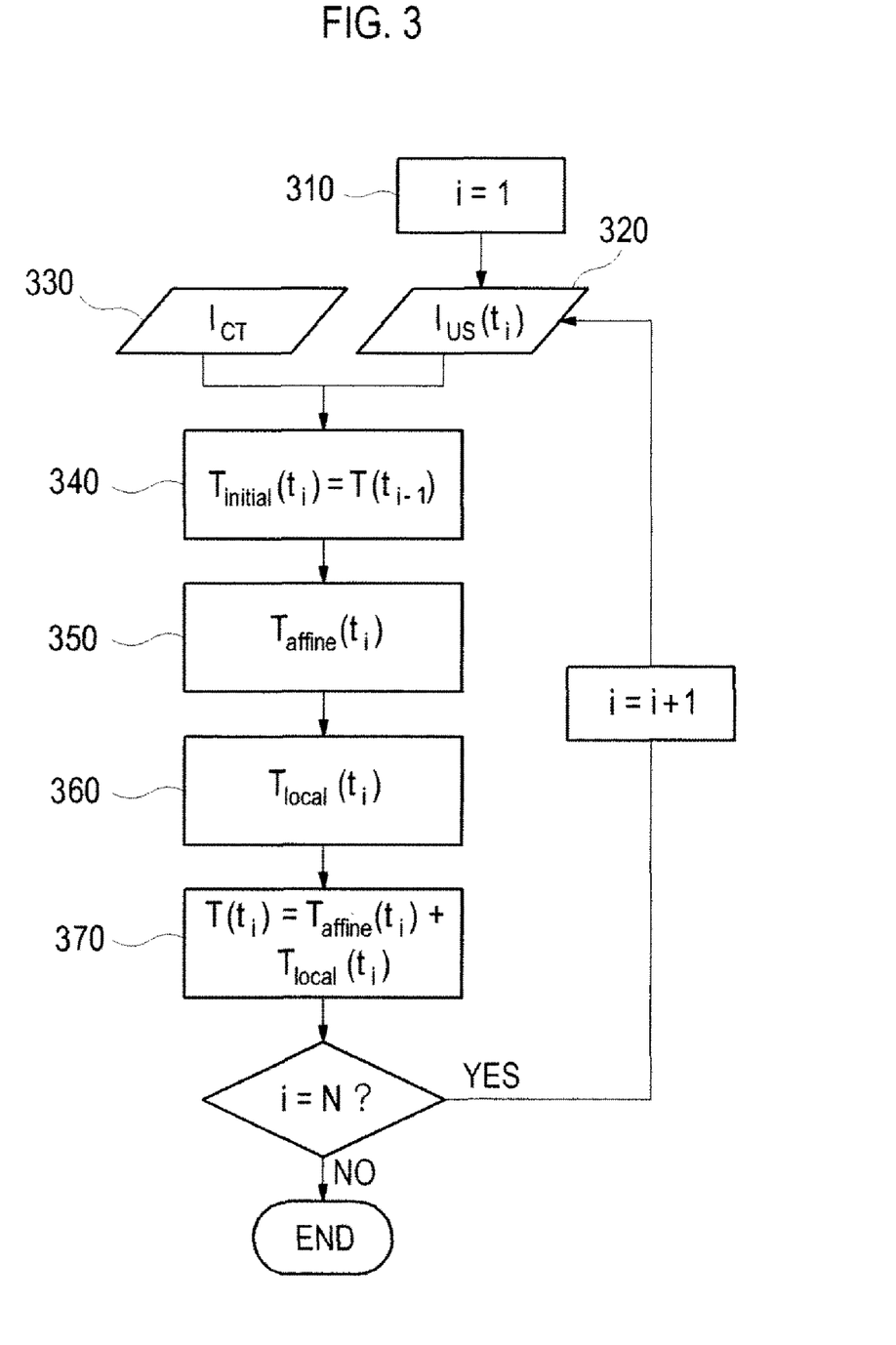
FIG. 3 is a flowchart showing a procedure of establishing registration functions.
Figure 4:
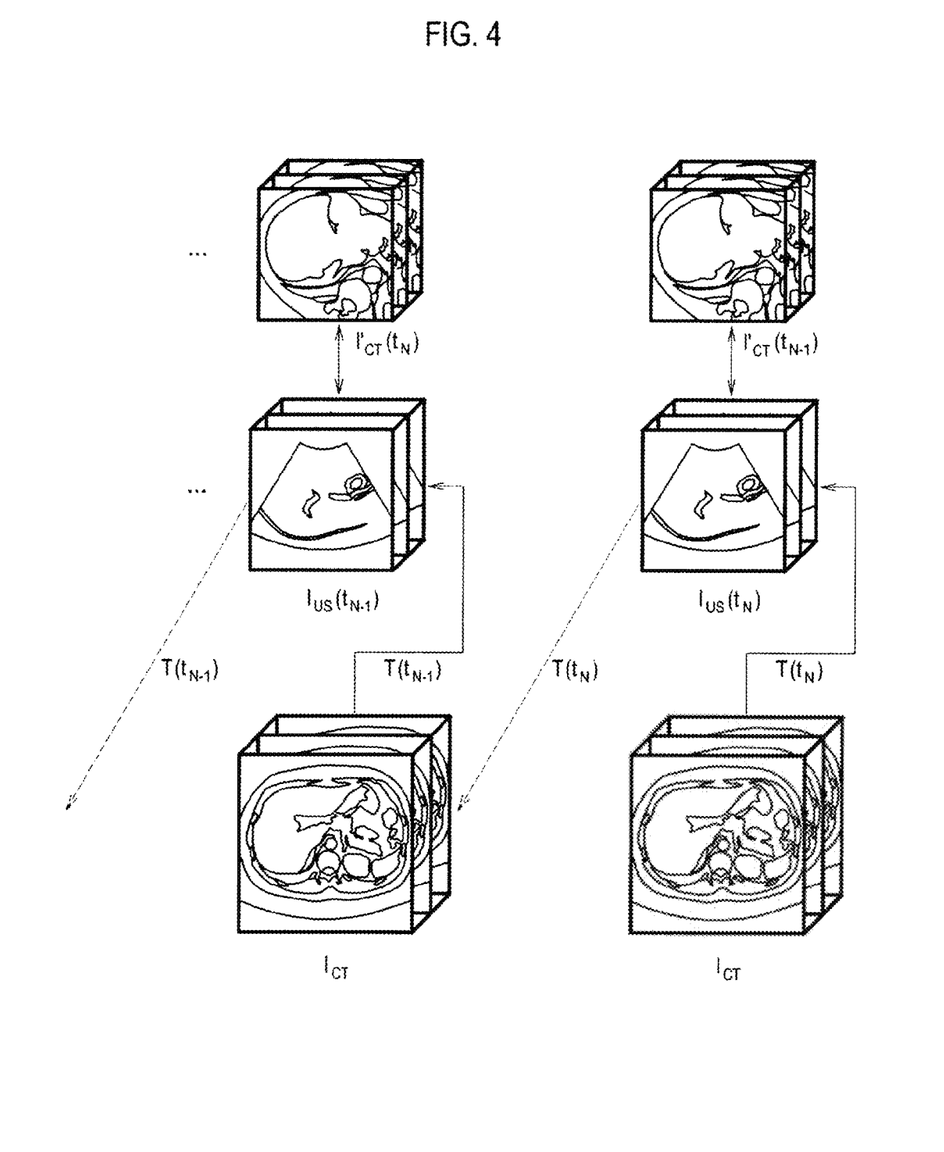
FIG. 4 is a schematic diagram showing an example of registration of a CT image onto ultrasound images.

Referring to FIG. 3, after performing the local registration at block 360, the affine transform function $T_{affine}$ and the local transform function $T_{local}$ may be summed to obtain a transform function $T(t_i)$ at block 370. The CT image $I_{CT}$ may be transformed by using the transform function $T(t_i)$ to obtain a CT image registered onto the ultrasound image $I'_{CT}(t_N)$ ("ultrasound-CT registered image") at each interval of the respiration. The ultrasound-CT registered images $I'_{CT}(t_N)$ at respective intervals of the respiration may be stored in the storage unit 140. The above process 320-370 may be repeatedly carried out upon all the ultrasound images obtained at the preoperative stage.

Figure 6:
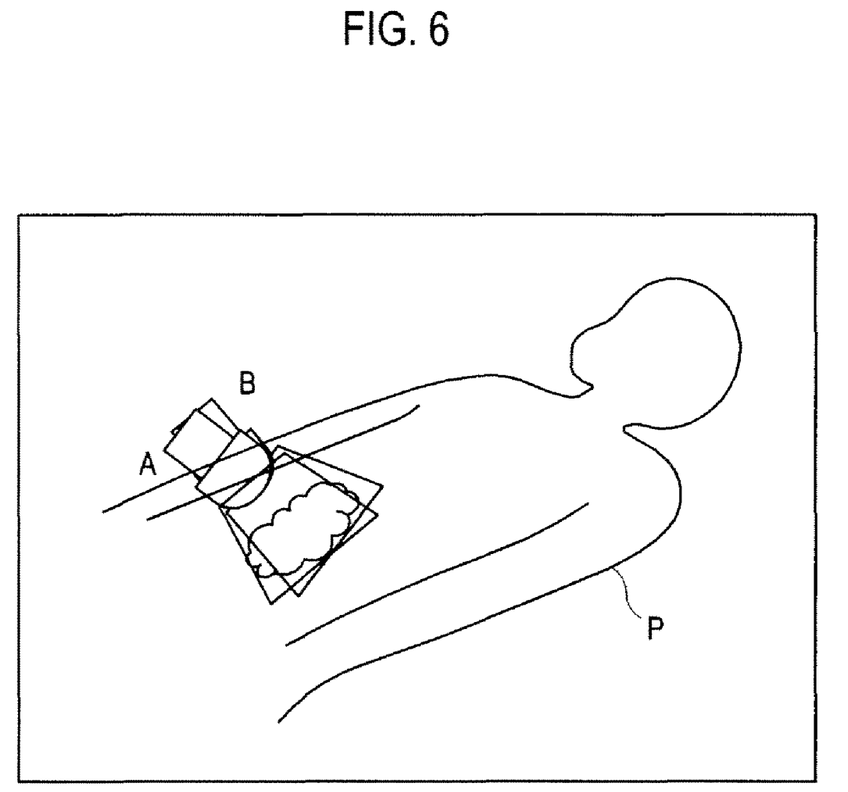
FIG. 6 is a schematic diagram showing an example of probe movement between a preoperative stage and an intraoperative stage.

At the intraoperative stage, once the probe placed at the first position A at the preoperative stage is moved to the second position B adjacent to the first position A as shown in FIG. 6, a rigid motion calibration function $T_{rigid}$ may be established for calibrating a position difference between the first position A and the second position B. In one embodiment, an ultrasound image obtained at the maximum inspiration at the preoperative stage may be set to a reference ultrasound image. The calibration unit 150 may be configured to measure similarities of the reference ultrasound image to the ultrasound images obtained at the preoperative stage. A first candidate image and a second candidate image may be selected based on the order of the measured similarities among the ultrasound images obtained at the respective intervals of the respiration. The calibration unit 150 may be configured to use the reference ultrasound image, the first candidate image and the second candidate image to determine a rigid transformation parameter, which produces maximal similarity, to thereby establish a calibration function $T_{rigid}$. The calibration function $T_{rigid}$ may be applied to the ultrasound images obtained at the preoperative stage and the ultrasound-CT registered images to perform the calibration of the probe movement.

Figure 7:
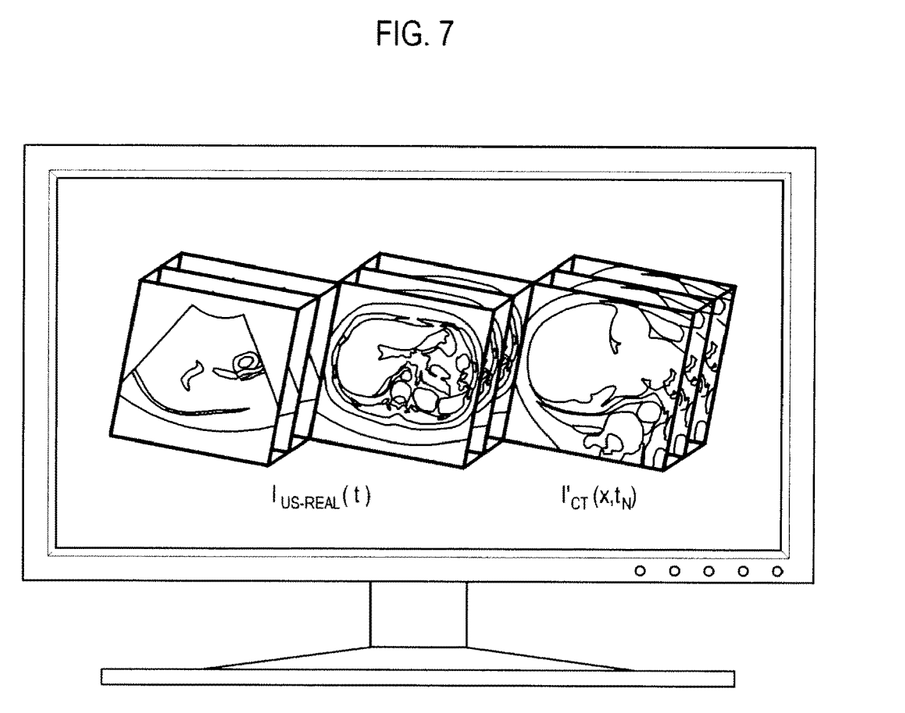
FIG. 7 is a schematic diagram showing an example of displaying a real-time ultrasound image and an ultrasound-CT registered image.

At the intraoperative stage, real-time ultrasound images may be acquired. Further, ultrasound images, which are most similar to the real-time ultrasound images $I_{US\text{-}REAL}(t)$, may be selected among the ultrasound images with the probe movement calibrated. An ultrasound-CT registered image corresponding to the selected ultrasound image may be retrieved. The real-time ultrasound image $I_{US\text{-}REAL}(t)$ and the retrieved ultrasound-CT registered image $I'_{CT}(x, t_N)$ may be displayed at the same time on a display unit 160, as shown in FIG. 7. In one embodiment, the display unit 160 may display the real-time ultrasound image and the ultrasound-CT registered image with superimposed or fused.

In one embodiment, the rigid motion calibration function is applied to the ultrasound images obtained at the preoperative stage and the registered images by considering the probe movement at the preoperative stage and the intraoperative stage. However, if the position of the probe is not changed at the preoperative stage and the intraoperative stage, then the application of the rigid motion calibration function may be omitted.

In another embodiment, the calibration unit 150 may be configured to select ultrasound images in the order of the measured similarity among the ultrasound images obtained at the respective intervals of the respiration. The calibration unit 150 may be configured to retrieve the ultrasound-CT registered image corresponding to the respective selected ultrasound images. The calibration unit 150 may be configured to perform interpolation upon the retrieved ultrasound-CT registered images. The display unit 160 may display the real-time ultrasound images obtained at the intraoperative stage together with the interpolated ultrasound-CT registered images.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A system for registering a computerized tomography (CT) image onto ultrasound images, comprising:
   an ultrasound image forming unit configured to sequentially form a plurality of first ultrasound images during a first predetermined cycle;
   a CT image forming unit configured to form a CT image during the first predetermined cycle;
   a registration unit configured to register the CT image onto the first ultrasound images to thereby form ultrasound-CT registered images;
   a storage unit configured to store the ultrasound-CT registered images,
   wherein the ultrasound forming unit is further configured to sequentially form a plurality of second ultrasound images during a second predetermined cycle, and
   wherein the registration unit is further configured to measure similarities between the first ultrasound images and the second ultrasound images and retrieve from the storage unit ultrasound-CT registered images each corresponding to the first ultrasound image having a highest similarity to each of the second ultrasound images; and
   a display unit configured to display the retrieved ultrasound image and the second ultrasound image.

2. The system of claim 1, wherein the first and second predetermined cycles are a respiratory cycle, the first ultrasound images being formed at a predetermined interval for the respiratory cycle and the CT image being obtained at a maximum inspiration.

3. The system of claim 2, wherein the registration unit is configured to:
   perform an affine registration of the CT image onto each of the first ultrasound images to thereby obtain an affine transform function;
   perform a local registration of the CT image onto each of the first ultrasound images to thereby obtain a local transform function; and
   transform the CT image based on the affine transform function and the local transform function to form the ultrasound-CT registered images.

4. The system of claim 3, wherein the registration unit is further configured to perform the affine registration to acquire the affine transform function, extract a set of common feature points from each of the first ultrasound images and the CT image, and obtain the affine transform function with integrated closet point algorithm using the set of common feature points.

5. The system of claim 4, wherein the registration unit is further configured to:
   perform the local registration of the CT image onto each of the first ultrasound images to obtain the local transform function;
   perform diaphragm extraction and vessel segmentation upon the CT image;
   perform a masking process to select boundary regions based on results from the diaphragm extraction and the vessel segmentation;
   extract gradient vectors and brightness values from the masked CT image and the ultrasound images; and
   measure similarities based on the gradient vectors and the brightness values to perform the local registration and to obtain a local transform function.

6. The system of claim 1, wherein the registration unit is further configured to select two or more ultrasound images from the first ultrasound image in an order of the similarities and retrieve ultrasound-CT registered images each corresponding to each of the selected ultrasound images, the registration unit being further configured to interpolate the retrieved ultrasound-CT registered images to form interpolated ultrasound-CT registered images.

7. The system of claim 1, wherein the ultrasound image forming unit includes a probe for transmitting and receiving ultrasound signals, the system further comprising a calibration unit configured to establish a calibration function based on a probe movement, wherein the calibration unit is further configured to apply the calibration function to the first ultrasound images and the ultrasound-CT registered images to form calibrated first ultrasound images and ultrasound-CT registered images.

8. The system of claim 7, wherein the ultrasound image forming unit is configured to form the first ultrasound images when the probe is placed at a first position and the second ultrasound images when the probe is placed at a second position, and wherein the calibration unit is configured to establish the calibration function based on differences between the first and second ultrasound images.

9. The system of claim 8, wherein the ultrasound forming unit is further configured to form a plurality of third ultrasound images in real time,
   wherein the registration unit is further configured to measure similarities between the first ultrasound images and the third ultrasound images, select two or more ultrasound images from the first ultrasound image in an order of the similarities, and retrieve ultrasound-CT registered images corresponding to the selected ultrasound images, the registration unit being further configured to interpolate the retrieved ultrasound-CT registered images to form interpolated ultrasound-CT registered images.

10. The system of claim 9, wherein a display unit is configured to display the retrieved ultrasound image and the third ultrasound image.

11. A method of registering a computerized tomography (CT) image to ultrasound image, comprising:
  a) sequentially forming a plurality of first ultrasound images during a first predetermined cycle;
  b) forming a CT image obtained during the first predetermined cycle;
  c) registering the CT image onto the first ultrasound images to thereby form ultrasound-CT registered images;
  d) storing the ultrasound-CT registered images;
  e) sequentially forming a plurality of second ultrasound images during a second predetermined cycle;
  f) measuring similarities between the first ultrasound images and the second ultrasound images and retrieving the ultrasound-CT registered images, each corresponding to each of the first ultrasound images having highest similarity to the second ultrasound image; and
  g) displaying the retrieved ultrasound image and the second ultrasound image.

12. The method of claim 11, wherein the first and second predetermined cycles are a respiratory cycle, the first ultrasound images being formed at a predetermined interval for the respiratory cycle and the CT image being obtained at a maximum inspiration.

13. The method of claim 12, wherein the c) includes:
  c1) performing an affine registration of the CT image onto each of the first ultrasound images to thereby obtain an affine transform function;
  c2) performing a local registration of the CT image onto each of the first ultrasound images to thereby obtain a local transform function; and
  c3) transforming the CT image based on the affine transform function and the local transform function to form the ultrasound-CT registered images.

14. The method of claim 13, wherein the c1) includes:
  performing the affine registration to acquire the affine transform function;
  extracting a set of common feature points from each of the first ultrasound images and the CT image; and
  obtaining the affine transform function with integrated closet point algorithm using the set of common feature points.

15. The method of claim 14, wherein the c2) includes:
  performing the local registration of the CT image onto each of the first ultrasound images to obtain the local transform function;
  performing diaphragm extraction and vessel segmentation upon the CT image;
  performing a masking process upon the CT image and the ultrasound images to select boundary regions based on results from the diaphragm extraction and the vessel segmentation;
  extracting gradient vectors and brightness values from the masked CT image and the ultrasound images; and
  measuring a similarity based on the gradient vectors and the brightness values to perform the local registration and to obtain a local transform function.

16. The method of claim 11, further comprising:
  selecting two or more ultrasound images from the first ultrasound image in an order of the similarity;
  retrieving ultrasound-CT registered images corresponding to the selected ultrasound images; and
  interpolating the retrieved ultrasound-CT registered images to form interpolated ultrasound-CT registered images.

17. The method of claim 11, further comprising:
  establishing a calibration function based on a probe movement;
  applying the calibration function to the first ultrasound images and the ultrasound-CT registered images to form calibrated first ultrasound images and ultrasound-CT registered images.

18. The method of claim 17, wherein the first ultrasound images are formed when the probe is placed at a first position and the second ultrasound images are formed when the probe is placed at a second position, and wherein the calibration function is established based on differences between the first and second ultrasound images.

19. The method of claim 18, further comprising:
  forming a plurality of third ultrasound images in real time at an intraoperative stage,
  measuring similarity between the first ultrasound images and the third ultrasound images;
  selecting two or more ultrasound images from the first ultrasound image in an order of the similarity;
  retrieving ultrasound-CT registered images corresponding to the selected ultrasound images; and
  interpolating the retrieved ultrasound-CT registered images to form interpolated ultrasound-CT registered images.

20. The method of claim 19, further comprising displaying the retrieved ultrasound image and the third ultrasound images.

* * * * *